(12) United States Patent
Laufer

(10) Patent No.: US 9,084,651 B2
(45) Date of Patent: Jul. 21, 2015

(54) DENTAL MICRO-TORNADO TISSUE CUTTING AND REMOVAL METHOD AND APPARATUS

(71) Applicant: Zohar Laufer, Johns Creek, GA (US)

(72) Inventor: Zohar Laufer, Johns Creek, GA (US)

( * ) Notice: Subject to any disclaimer, the term of this patent is extended or adjusted under 35 U.S.C. 154(b) by 2 days.

(21) Appl. No.: 14/028,587

(22) Filed: Sep. 17, 2013

(65) Prior Publication Data

US 2014/0080090 A1    Mar. 20, 2014

Related U.S. Application Data

(60) Provisional application No. 61/701,947, filed on Sep. 17, 2012.

(51) Int. Cl.
| | |
|---|---|
| *A61C 3/025* | (2006.01) |
| *A61C 17/02* | (2006.01) |
| *A61C 5/02* | (2006.01) |
| *A61C 17/06* | (2006.01) |
| *A61C 1/00* | (2006.01) |

(52) U.S. Cl.
CPC . *A61C 3/025* (2013.01); *A61C 5/02* (2013.01); *A61C 17/0202* (2013.01); *A61C 17/0208* (2013.01); *A61C 17/046* (2013.01); *A61C 1/0061* (2013.01)

(58) Field of Classification Search
CPC ....... A61C 3/025; A61C 5/02; A61C 17/0208
USPC .......... 433/88; 451/2–3, 36–40, 75–102, 456; 606/131
See application file for complete search history.

(56) References Cited

U.S. PATENT DOCUMENTS

| | | | |
|---|---|---|---|
| 4,021,921 A * | 5/1977 | Detaille | 433/81 |
| 4,294,251 A * | 10/1981 | Greenwald et al. | 604/28 |
| 5,334,016 A | 8/1994 | Goldsmith et al. | |
| 5,334,019 A | 8/1994 | Goldsmith et al. | |
| 5,820,373 A | 10/1998 | Asai et al. | |
| 6,093,021 A | 7/2000 | Rainey | |
| 6,106,288 A | 8/2000 | Annett et al. | |
| 6,179,614 B1 | 1/2001 | Elrod et al. | |
| 6,224,378 B1 | 5/2001 | Valdes et al. | |
| 6,309,217 B1 | 10/2001 | Aumuller | |
| 6,497,572 B2 | 12/2002 | Hood et al. | |
| 6,799,968 B2 | 10/2004 | Aumuller et al. | |
| 7,090,568 B2 * | 8/2006 | Kreiselmaier et al. | 451/102 |
| 7,901,373 B2 | 3/2011 | Tavger | |
| 8,002,544 B2 | 8/2011 | Rizoiu et al. | |
| 8,043,088 B2 | 10/2011 | Johnson | |
| 8,221,117 B2 | 7/2012 | Rizoiu et al. | |
| 8,388,345 B2 | 3/2013 | Ruddle | |
| 2006/0257819 A1 | 11/2006 | Johnson | |
| 2007/0148615 A1 | 6/2007 | Pond | |
| 2007/0248932 A1 | 10/2007 | Gharib et al. | |
| 2008/0044789 A1 | 2/2008 | Johnson | |
| 2009/0130622 A1 | 5/2009 | Bollinger et al. | |

(Continued)

*Primary Examiner* — Edward Moran

(57) ABSTRACT

A method and apparatus is disclosed for treating teeth associated with tooth structure removal and disinfection, in particular for endodontic procedures such as root canal tissue removal and decay treatment. Traditional methods involve the use of files, reamers, chemicals, drills, and burs, which have many disadvantages. The disclosed method and apparatus are based on the use of micro-tornado forces generated in a small working head attached to a dental hand piece and discharged from an extended cannula into a root canal orifice or a cavity to abrade, cut, and remove the content.

27 Claims, 11 Drawing Sheets

(56) References Cited

U.S. PATENT DOCUMENTS

| | | |
|---|---|---|
| 2010/0092922 A1 | 4/2010 | Ruddle |
| 2010/0152634 A1 | 6/2010 | Dove |
| 2011/0111365 A1 | 5/2011 | Bergehim et al. |
| 2011/0117517 A1 | 5/2011 | Bergheim et al. |
| 2013/0288195 A1* | 10/2013 | Mueller, Daniel ............ 433/88 |
| 2015/0044631 A1* | 2/2015 | Lifshitz et al. ................ 433/81 |

* cited by examiner

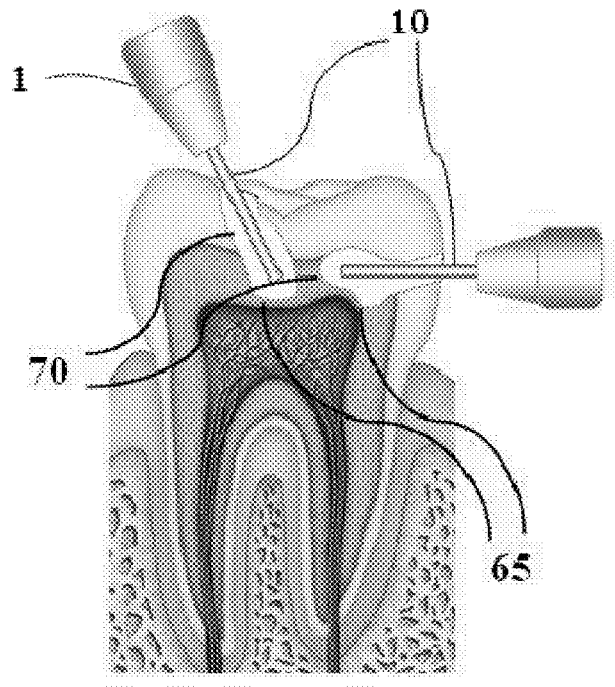
FIG. 8C
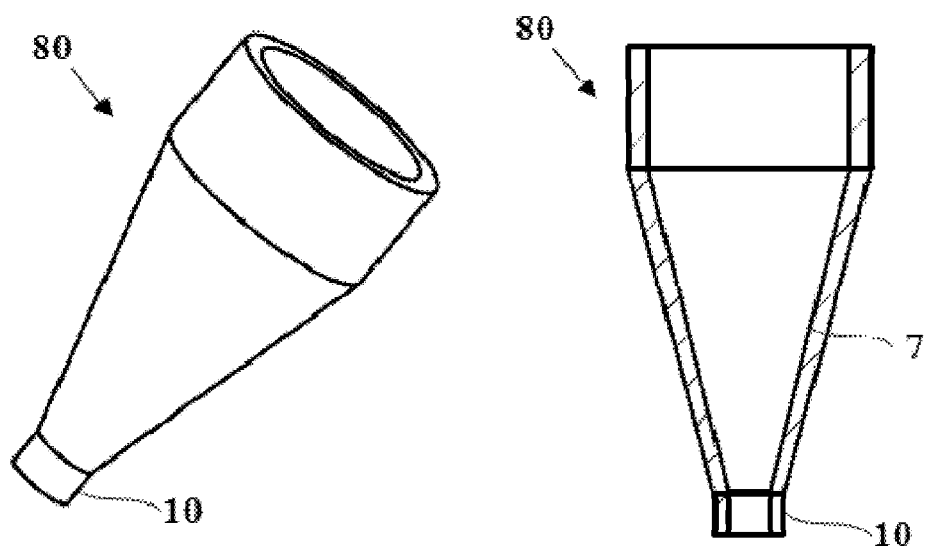
FIG. 9A  FIG. 9B

DENTAL MICRO-TORNADO TISSUE CUTTING AND REMOVAL METHOD AND APPARATUS

CROSS-REFERENCE TO RELATED APPLICATIONS

This application claims benefit of U.S. Provisional Application No. 61/701,947, filed Sep. 17, 2012, which is hereby incorporated herein by reference in its entirety.

TECHNICAL FIELD

The present invention generally relates to dental instrumentation used for cutting, cleaning, and removal of necrotic tissues, in particular in root canal therapy or in decay therapy.

BACKGROUND

For over 200 years, the dental root canal procedure has been done using root canal files, which are tiny tapered drills sized according to the size and shape of the canal in order to remove mostly necrotic tissues while enlarging the canal walls to prepare it for obturation, tissue dissolving chemicals, disinfection, and drying. These files are inserted into the canal after the pulp chamber has been accessed and the canal's orifice has been discovered. The cleaning procedure is executed by pushing, rotating, and pulling the file containing debris out, while irrigating with dissolving chemicals such as sodium hypochlorite and EDTA to assist with softening and dissolving the tissues. This cleaning procedure is repeated with a different file sizes and finalized by dissolving the smear layer, which contains debris such as tissue and bacteria, to uncover the dentine tubules. The tubules may also be contaminated, so they also need to be disinfected in order to prevent a retreatment in the future, i.e., the major criteria for a successful treatment.

This traditional procedure has many disadvantages and risks, such as broken file left inside the canal, wall perforation, tooth cracking, and chemical poisoning. Even though advanced tools, such as rotary and retractable activators are in use, files and chemicals still end up being used inside the canal. In addition, the use of a drill or bur causes a disturbing sound that causes patient anxiety.

In addition, cavity preparation often requires removing healthy tooth structures to reach hidden or hard to reach cavity formations, resulting in a weaker tooth structure. In cleaning a cavity with a bur, if the pulp chamber is penetrated a root canal procedure becomes necessary. Removing as little healthy tooth structure as possible is desirable.

SUMMARY

The disclosed methods and apparatus overcome disadvantages of traditional instrumentation by using micro-tornado forces applied within a tiny cannula and aimed toward necrotic tissue. This approach allows the user to differentiate soft and hard tissue according to adjustable preset forces.

A dental instrument is disclosed that comprises a working head that generates micro-tornado forces for cutting, cleaning, and/or removal of necrotic tissues. In some embodiments, the dental instrument comprises a fluid inlet, one or more orifices configured to intensify the linear velocity of the fluid, a vortexing chamber configured to convert the linear velocity of the fluid to a rotational velocity of at least 6,000 rpm, and a cannula at the distal end of the working head fluidly connected to the vortexing chamber. For example, the fluid can be pressurized air comprising abrasive powder or fluid particles suspended therein. The dental instrument can further comprise a source of negative pressure beyond the end of the cannula. In some of these embodiments, the vortexing chamber comprises a conical shape with a base and an apex, wherein the one or more orifices are positioned as the base of the conical shape, and wherein the apex is posited at the distal end of the working head.

The working head can comprise an outer portion and an inner portion that together define a conical gap between the inner surface of the outer portion and the outer surface of the inner portion, wherein the conical gap has a base and an apex, wherein the apex is at the distal end of the working head. The working head can further comprises one or more orifices positioned at the base of the conical gap and fluidly connected to a tube supplying a pressurized gas mixture (pressurized mixture supply tube) configured to intensify the velocity of the pressurized gas mixture. The working head can further comprise one or more sloped down grooves configured to direct the pressurized gas mixture from the one or more orifices in a conical spiral toward the apex of the conical gap. The working head can further comprise a cannula at the distal end of the working head fluidly connected to the conical gap. In some cases, the cannula is curved (or can be bent). The disclosed dental instrument can also contain a hand piece connected to the proximal end of the working head.

In some embodiments, the dental instrument further comprises a suction tube extending distally through the center and beyond the end of the cannula. For example, the suction tube can be fluidly connected to a suction pump to remove tissue, fluid, and/or abrading particle residue. In some cases, the suction tube extends through the center of the inner portion and out the proximal end of the working head. In some cases, the suction tube comprises a sharpened edge or teeth.

The pressurized mixture supply tube can be fluidly connected to a gas and abrasive powder mixing chamber. In some embodiments, the gas and abrasive powder mixing chamber comprises a motorized feeder configured to feed controlled amounts of abrasive powder into a pressurized gas and powder mixing tube to produce a gas and powder mixture, wherein the pressurized gas mixing tube is fluidly connected to the pressurized mixture supply tube. For example, the motorized feeder can be a rotating helix feeder. The gas and abrasive powder mixing chamber can also contain a hopper configured to feed the abrasive powder into the motorized feeder. In addition, the pressurized gas mixing tube can comprise a pressure equalizing hole configured to release the gas and powder mixture into the hopper in an amount sufficient to maintain pressure equilibrium.

The pressurized mixture supply tube can also be connected to a gas and fluid mixing chamber. In some embodiments, the gas and fluid mixing chamber comprises a pressurized gas and fluid mixing tube fluidly connected to the pressurized mixture supply tube, and a cannula fluidly connected to a fluid compartment, wherein the cannula is positioned in a constriction within the pressurized gas and fluid mixing tube configured to cause a sufficient venturi effect to draw fluid out of the fluid chamber and create a mist. In some cases, the pressurized gas and fluid mixing tube comprises a pressure equalizing hole configured to release the mist into the fluid chamber in an amount sufficient to maintain pressure equilibrium.

In some cases, the pressurized mixture supply tube is fluidly connected to both a gas and powder mixing chamber and a gas and fluid mixing chamber by one or more check valves, selector valves, or combinations thereof.

Examples of suitable abrasive powders include aluminum oxide, silica, or glass powder from approximately 200 to 300 grit. In some cases, the pressurized gas is air. Examples of suitable fluids that can be used include distilled water, EDTA, and anti-bacteria solutions.

The dental instrument can optionally have an aspiration cap configured to collect tissue, fluid, and/or abrading particle residue. For example, the aspiration cap can contain a dome affixed to the proximal end of the working head. The aspiration cap can also contain a perforated aspiration tube fluidly connected to the suction tube.

The dimensions of the dental instrument include those suitable for dental and endodontic procedures, including root canals. For example, in some embodiments, the cannula is about 1 mm to about 20 mm in length; the conical gap is about 1.0 to about 2.0 mm in width; the base of the conical gap is about 4.5 to about 5.5 mm in diameter; and the height of the conical gap from base to apex is about 5 to about 10 mm in length. The dimensions of the dental instrument can be adjusted for various length tooth crowns for access to the root canal orifice, or to reach decay structures. Further, the cannula may be curved to access pulp chambers or tooth decay structures.

One advantage of the disclosed dental instrument is the ability of the micro-tornado forces to follow soft tissue, even if it is curved. In contrast, traditional instruments can only follow straight lines. Moreover, the air pressure can be adjusted so that the gas mixtures preferentially cut, clean, and/or remove necrotic tissues without affecting healthy tissue. This combination of features allows the instrument to reach and remove all necrotic tissue in a space without affecting healthy tissue. In addition, whereas traditional instruments are often unable to remove hard tissues, such as calcifications, resulting in the need for extraction, the disclosed instrument can be adjusted to remove these hard tissues.

Also disclosed is a method for cutting and removing decayed tissue from a tooth. Non-limiting examples of decayed tissue include enamel, dentine, and pulp. The method can involve abrading the tissue with a pressurized gas and abrasive powder mixture. The method can further involve excavating the tissue, fluid, and/or abrasive particle residue, e.g., by suction. The method can further involve irrigating the tooth with a pressurized gas and liquid mixture under micro-tornado forces.

The micro-tornado forces can be generated by forcing the pressurized gas and abrading powder mixture or a pressurized gas and liquid mixture at high speed around a cone in a conical spiral from its base to its apex. In some embodiments, gas mixture is forced around the cone at a speed of at least 6,000 rpm. The pressurized gas and abrading powder mixture or a pressurized gas and liquid mixture under micro-tornado forces can be directed through a distal extended cannula toward the tooth structure.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 8A, FIG. 8B and FIG. 8C are a cross-section view of tooth decay (FIG. 8A) and cleaning results using a bur instrument (FIG. 8B) and the disclosed working head (FIG. 8C).

FIGS. 9A and 9B are perspective and cross-section views, respectively, of an embodiment of an outer portion of the working head.

DETAILED DESCRIPTION

Figure 1:
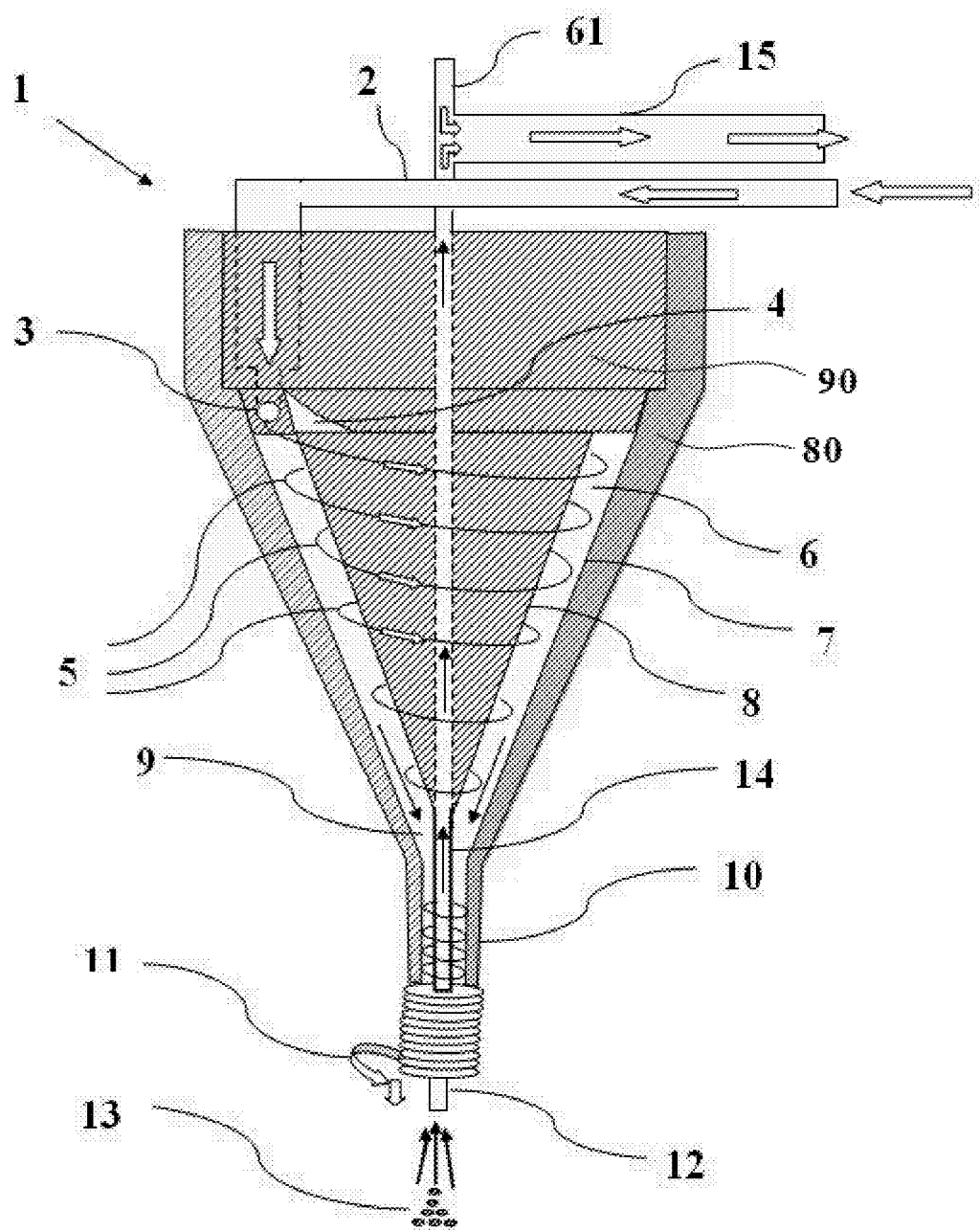
FIG. 1 is a cross-section view of an embodiment of a working head for generating micro-tornado forces.

Referring now to the Figures, FIG. 1 is cross-sectional view of a working head (1) capable of converting high pressure gas mixed with abrasive particles or gas mixed with fluid to micro-tornado forces. The term "micro-tornado" refers to a small column of air undergoing high speed rotation about an area of negative pressure. For example, the column of air can be from 0.1 to 5 mm in diameter, including about 0.4 mm to 2 mm diameter. The high speed rotation can be at least about 6,000 rpm, including at least about 10,000 rpm. In some embodiments, negative pressure is caused by suction at the center of the column. In other embodiments, however, the negative pressure is provided outside the column of air. In addition, centripetal force can be created by the area to be treated (e.g., walls of root canal).

The mixture is converted to high velocity and high speed rotations inside a conical space (6) and discharged throughout an extended cannula (10) as a centrifugal force (11). A high pressure gas mixed with abrading particles or fluid, or a mixture thereof, is provided from a pressurized mixture supply tube (2) into one or more small orifices (3) positioned towards a sloped down groove (4) and into a parallel conical gap (6) between an inner cone (8) and an outer conical wall (7), thereby converting the pressurized mixture to a high velocity stream and high speed rotation (5). The mixture is then forced to discharge (9) through the cannula nozzle (10), e.g., into a tooth root canal orifice, as a centrifugal and forward force (11) capable of abrading and departing tissues content.

As shown in FIG. 1, the working head can comprise an outer portion (80) and an inner portion (90) that assemble to define a conical gap between the inner surface (7) of the outer portion (80) and the outer surface (8) of the inner portion (90). These inner (7) and outer (8) surfaces defining the conical gap (6) are preferably made from a hard material with a polished surface. For example, the material can be a hardened stainless steel, tungsten carbide, or titanium. Other hard materials suitable for dental applications are known and adaptable in the present device. This material and the conical shape narrowing towards the discharging nozzle/cannula (10) minimizes friction and increases efficiency and performance by (a) allowing the sharp abrasive particles to skate around the gap without damaging their sharp edges and (b) increasing the velocity and speed of the rotation within the gap. The highest rotation speed is achieved at the smallest diameter at the bottom of the conical gap 6.

The working head (1) is also optionally connected to a suction pump (28) by a suction line (15), e.g., to excavate the abraded tissues and abrading particles (13). This suction line (15) can be connected to a suction tube (12) located in the center of the cannula (10) and preferably extending beyond the end of the cannula (10) (see FIG. 11). For example, the suction tube (12) can extend about 1 to about 3 mm beyond the end of the cannula (10). This suction line (15) can also produce the negative pressure needed to form the micro-tornado forces. In some embodiments, the suction tube (12) extends proximally through the midline of the inner portion 90 of the working head (1) through a centered inner suction tube (14) in order to connect to the suction line (15). In some embodiments, there is a further aspiration tube (61) connected to the suction line (15) (e.g., see FIG. 7)

Figure 2:
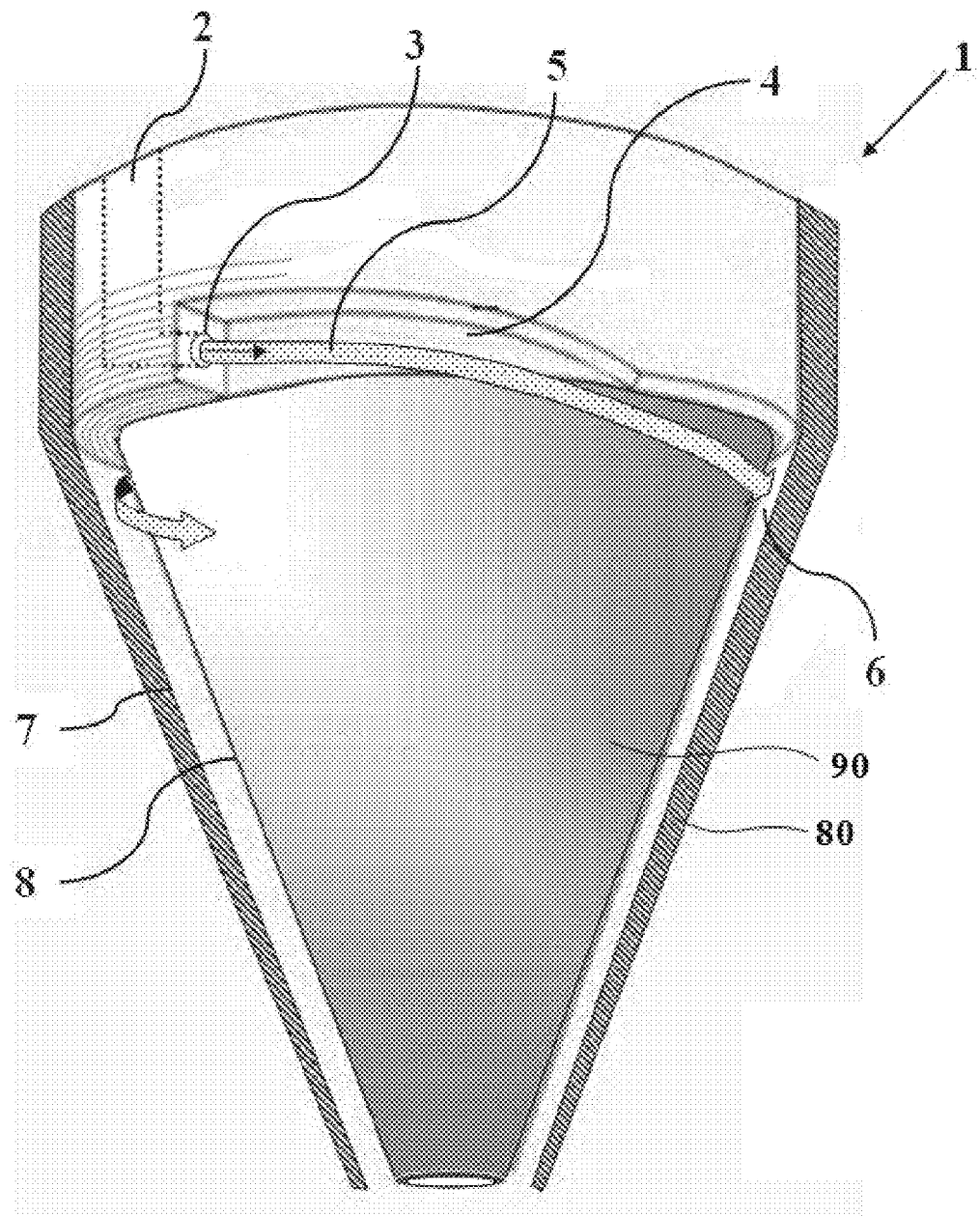
FIG. 2 is a partial cross-section view of the working head showing conversion of high pressure to high velocity and high speed rotation.

FIG. 2 is a partial cross-section view of the working head showing conversion of high pressure to high velocity and high speed rotation. When highly pressurized gas, e.g., containing abrading particles or fluid, or a mixture thereof, is provided from a pressurized mixture supply tube (2) discharged through one or more orifices (3), it transforms to high velocity flow. When this is guided by a sloped groove (4) and directed into the round conical gap (6) in a conical spiral, it results in high speed rotation inside the conical gap (6).

Note that while only one orifice (3) and one sloped groove (4) is shown in FIG. 1 and FIG. 2, the working head (1) can contain 2, 3, 4, 5, 6, or more orifices (3) and sloped grooves (4) feeding pressurized gas into the canonical gap (6).

Figure 3:
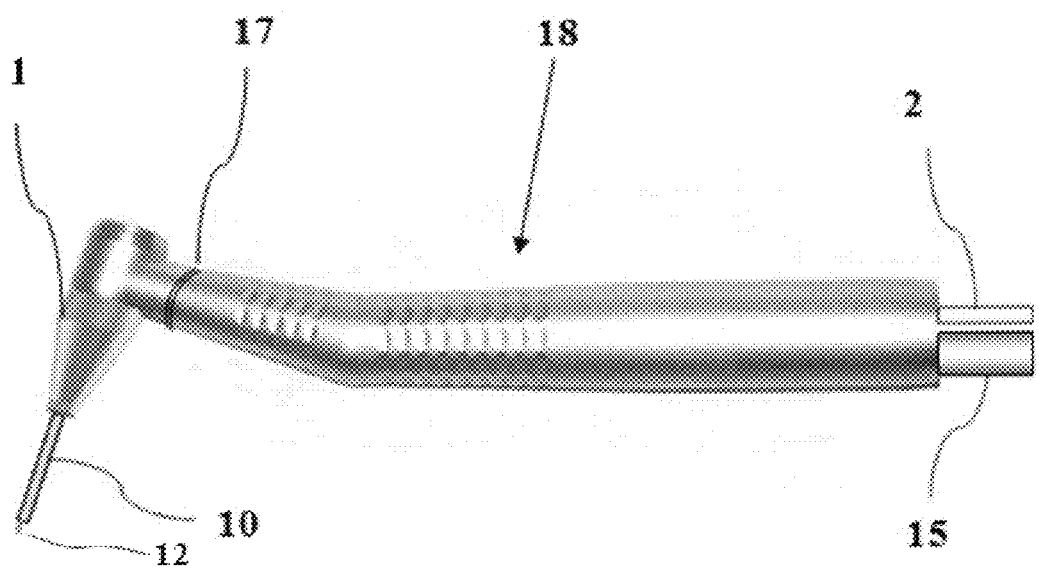
FIG. 3 is a picture of a working head connected to a hand piece.

FIG. 3 is a picture of a hand piece (18) connected to a working head (1) via fast coupling (17), a pressurized mixture supply tube (2), and a suction line (15).

Figure 4:
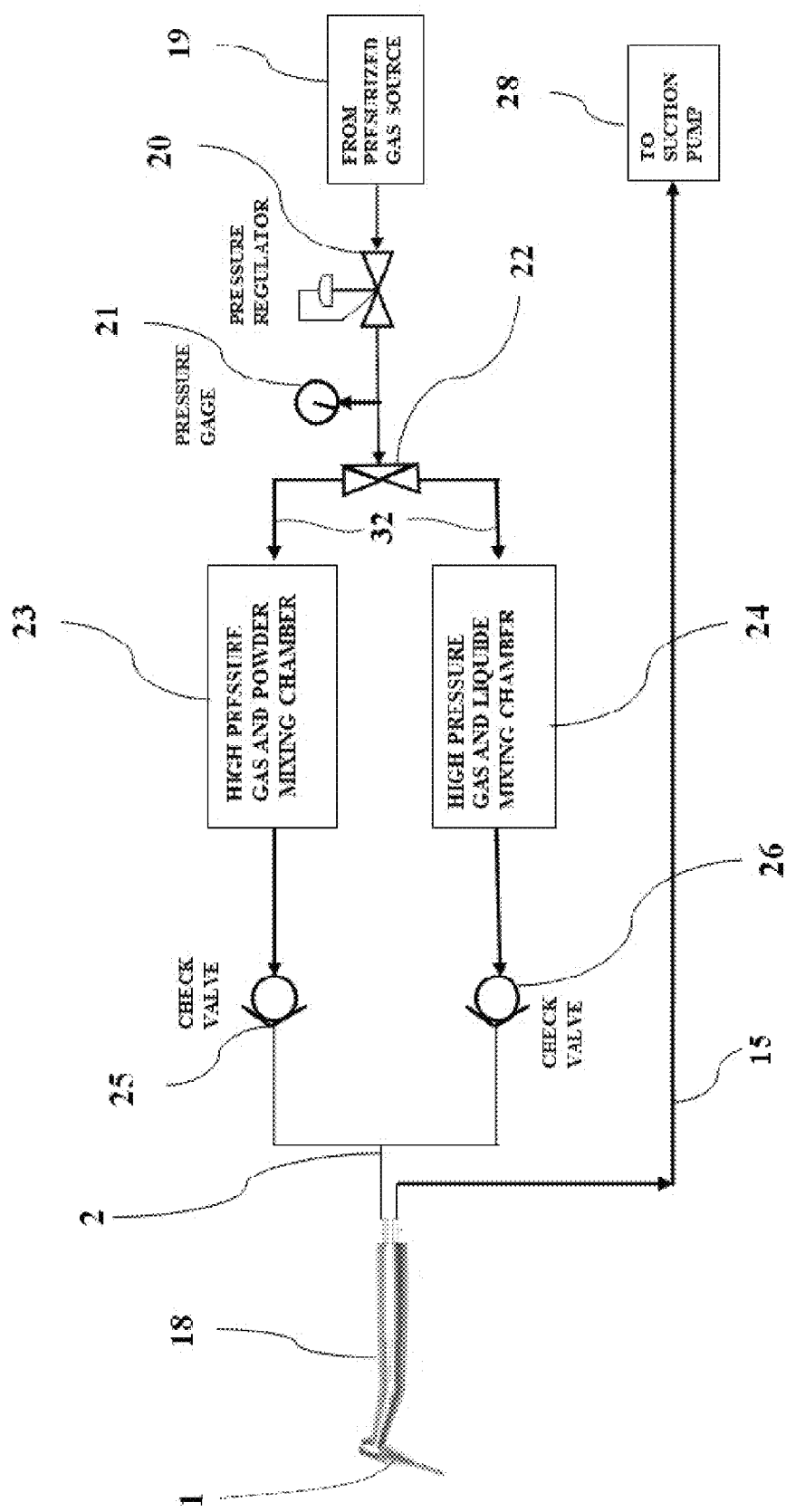
FIG. 4 is the schematic flow chart of the gas and suction components.

FIG. 4 is a flow chart showing connection of pressurized gas, abrasive mixture, liquid mixture, and suction components to a hand piece (18) and working head (1). In this embodiment, a high pressure gas source (19) is provided to a pressure regulator (20), pressure gage (21), and a selector valve (22). The selector valve (22) alternates connection of the gas source (19) to a high pressure gas and abrasive powder mixing chamber (23) or to a high pressure gas and fluid mixing chamber (24). The mixing chambers (23, 24) are connected to the pressurized mixture supply tube (2) via check valves (25, 26). The hand piece (18) is also connected to a suction pump (28) using a suction line (15).

Figure 5:
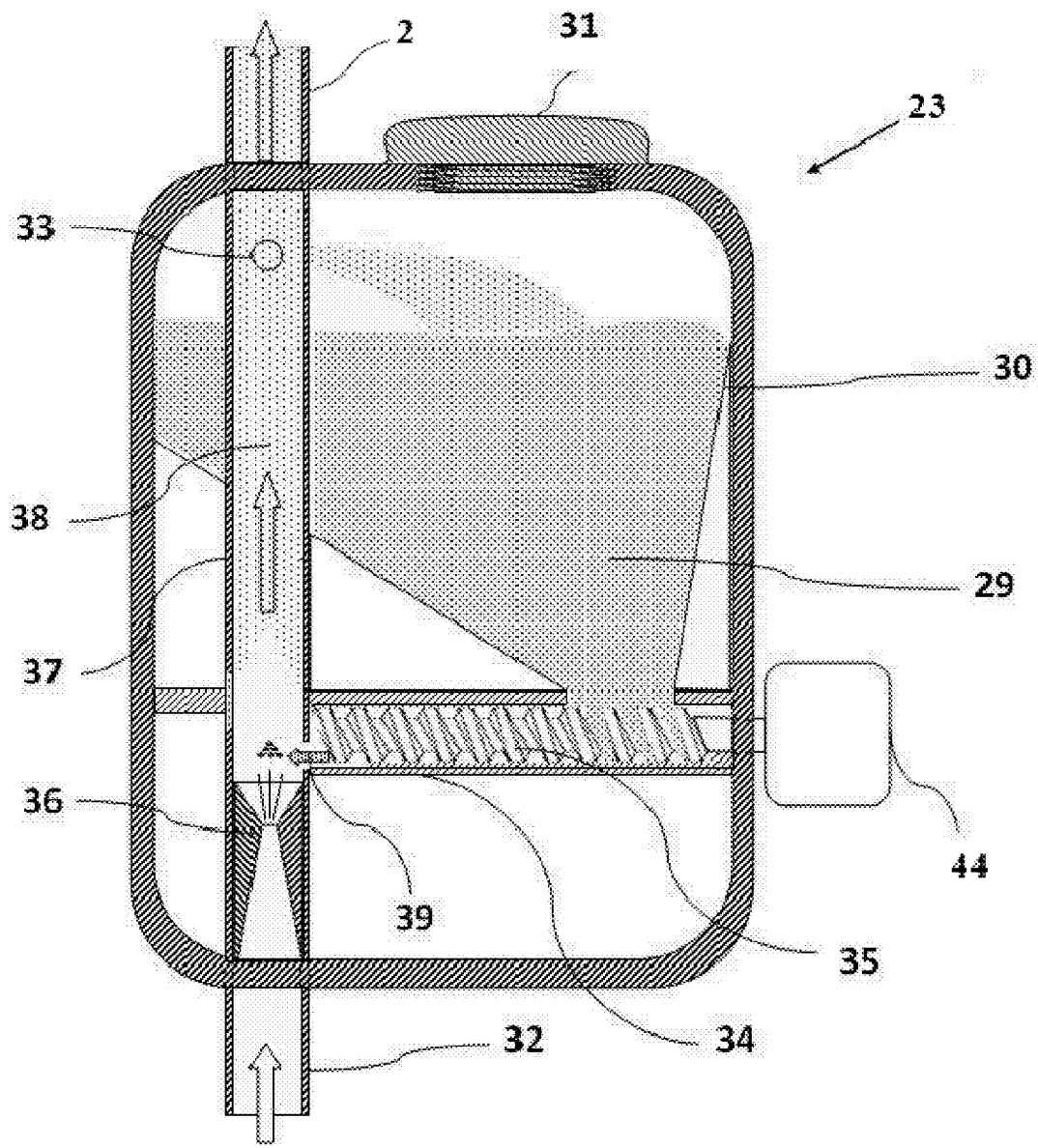
FIG. 5 is a cross-section view of a high pressure gas an abrading powder mixing chamber.

FIG. 5 is a cross-section view of a high pressure gas and abrading powder mixing chamber (23) as depicted in the flow chart of FIG. 4. In this embodiment, the chamber contains abrading powder (29) filled into a hopper 30 through an upper filling opening sealed with a pressure cap (31). The chamber contains a mixing tube (37), a feeding chamber (34), and a rotating helix feeder (35) connected to and driven by a speed controlled gear motor (44). A regulated gas pressure from the selector valve (22) is applied through a tube (32) forced up through a nozzle (36) where it is mixed with abrading particles (29) fed from an opening (39) delivered by the rotating feeder (35) rotated by the controlled speed gear motor (44) to delivering the desired amount of abrasive particles (29). The pressurized mixture (38) is provided through a check valve (25) to the pressurized mixture supply tube (2), hand piece (18), and working head (1). Some of the pressurized mixture (38) also passes through a pressure equalizing hole (33) back into the hopper (30).

Figure 6:
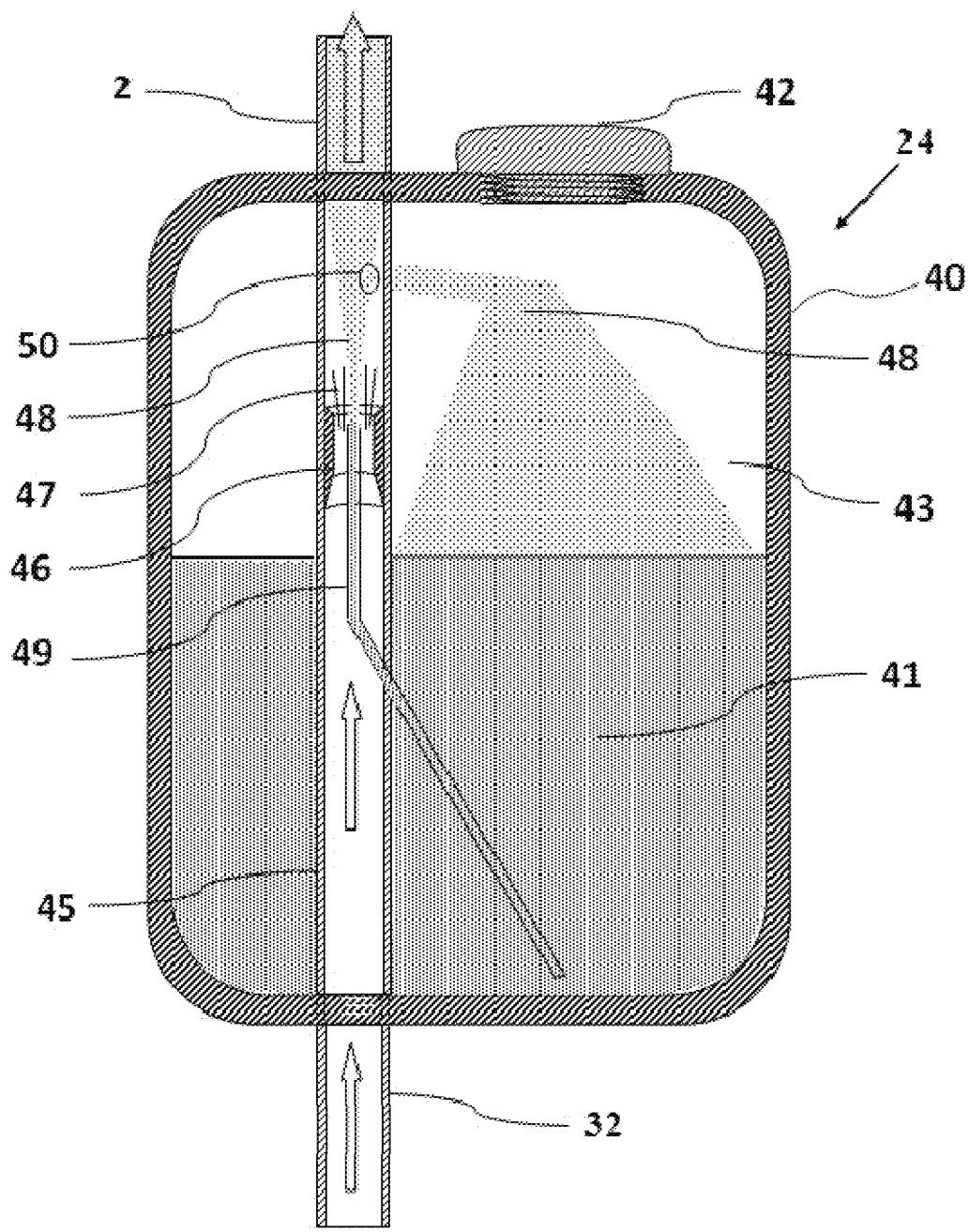
FIG. 6 is a cross-section view of a high pressure gas and fluid mixing chamber.

FIG. 6 is a cross-section view of the high pressure gas and fluid mixing chamber (24) as depicted in the flow chart of FIG. 4, creating a high pressure mist for rinsing the tooth (e.g., root canal). In this embodiment, a pressurized chamber (40) contains liquid (41) refillable from a top opening sealed with a cap (42) and pressurized gas (43) provided from selector valve (22) to the chamber tube (32), which is connected to an inner tube (45) that narrows at a narrowed part (46) creating a high velocity flow with a veturi effect (47). This venturi effect sucks fluid (41) from a cannula (49) creating a gas and fluid mixture (48) (mist) that is provided through a check valve (25) to the pressurized mixture supply tube (2), hand piece (18), and working head (1). Some of the highly pressurized gas and fluid mixture (48) passes through an opening (50) maintaining pressure in the fluid compartment (43).

Figure 7:
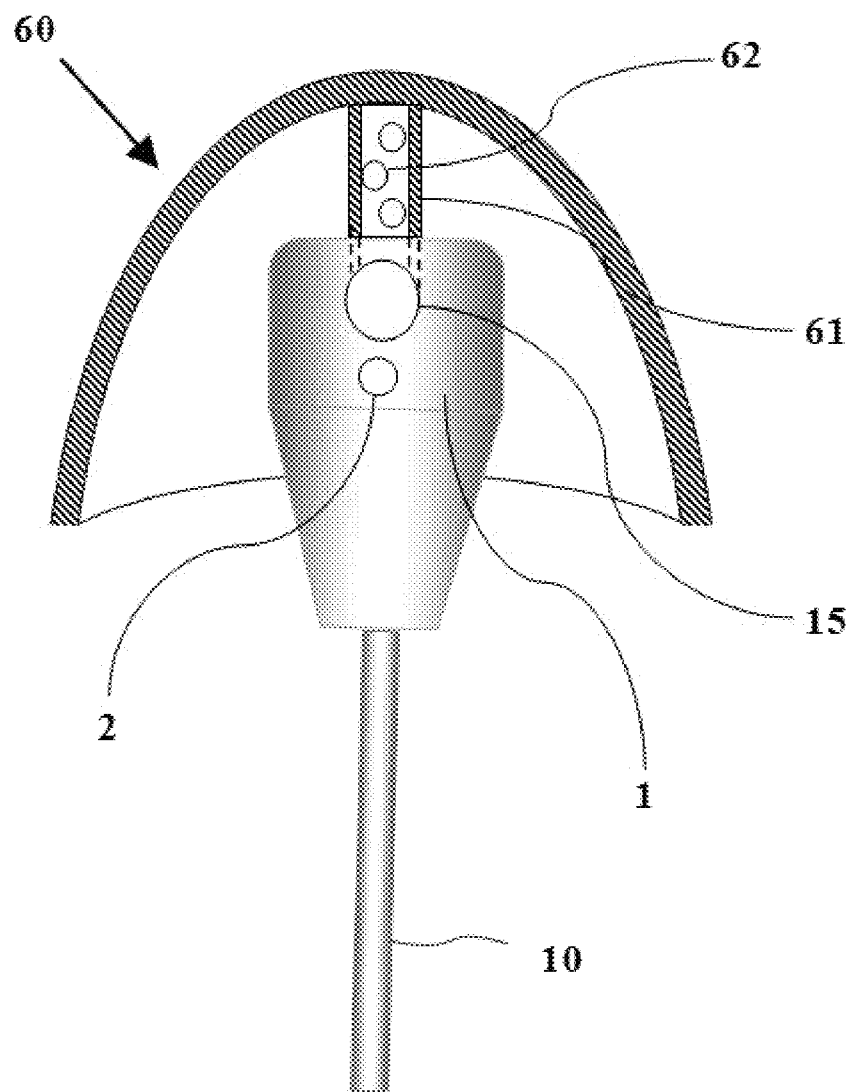
FIG. 7 is a cross-section view of an aspiration cap connected to the working head.

FIG. 7 is a partial cross-section view of an aspiration cap (60) connected to the working head (1). This cap (60) can collect residue of tissue, water, and/or abrading particles released from a tooth under treatment. In this embodiment, the cap (60) contains a round dome (58) connected to a perforated aspiration tube (61) with surrounding holes (55) attached to the proximal end of the working head (1) and into suction line (15). In some embodiments, the aspiration cap produces the negative pressure necessary to produce the micro-tornado forces, e.g., instead of or in addition to the suction tube.

Figure 8A:
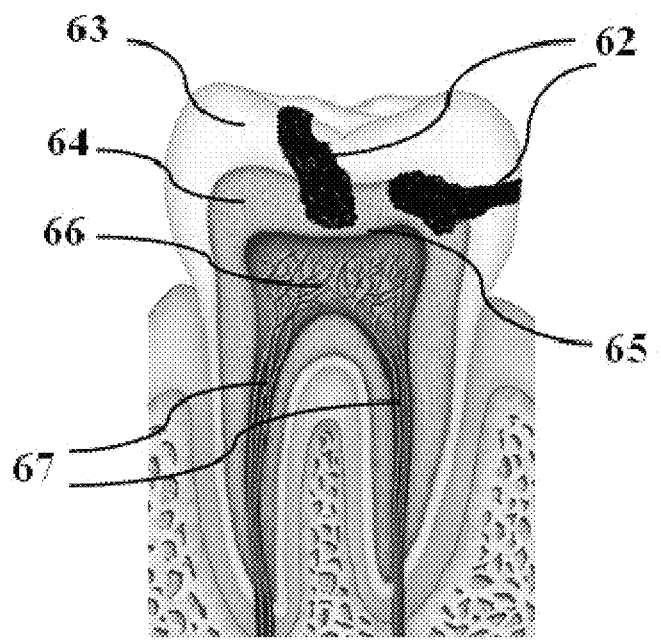
Figure 8B:
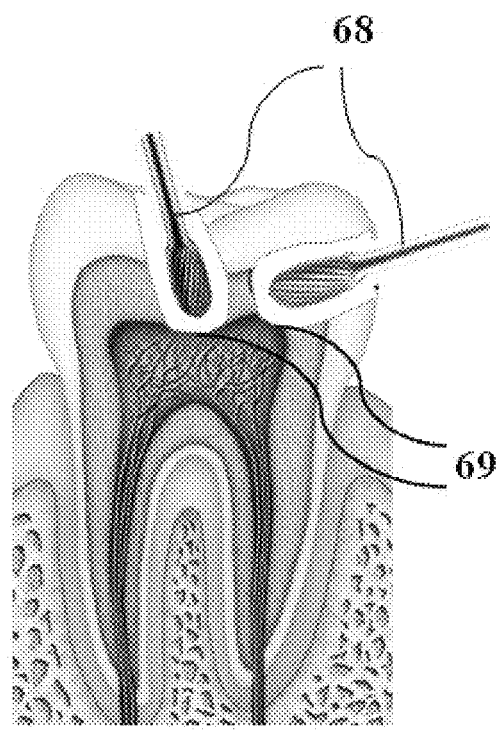

FIG. 8A is a cross-section view of tooth with decay (62), infected enamel (63), and infected dentine (64), but also with a healthy dentine layer (65) that protects healthy pulp (66) and healthy root canal tissues (67). As illustrated in FIG. 8B, cleaning the decay (62) with a dental bur (68) penetrated the healthy dentine layer (69) causing contamination of the healthy pulp (66) and root canal tissue (67). In contrast, FIG. 8C shows that when cleaning the same decay (62) with the disclosed working head (1) and cannula (10), the dentine layer (65) and the healthy pulp (66) remained intact. The cleaning area (80) is better controlled.

Figure 10:
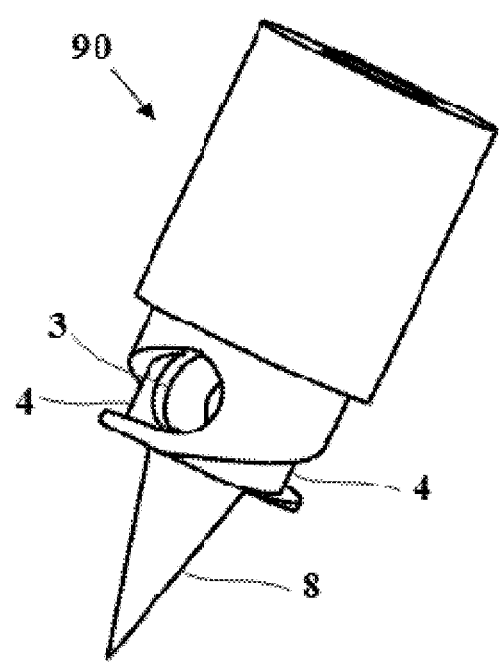
FIG. 10 is a perspective of an inner portion of an embodiment of the working head.

FIGS. 9A and 9B are perspective and cross-section views, respectively, of an example outer portion (80) of the working head. FIG. 9B shows the inner surface (7) of the outer portion (80) and the cannula (10). FIG. 10 is a perspective of an example inner portion (90) of a working head showing an orifice (3), one sloped groove (4), and an inner cone (8).

Figure 11:
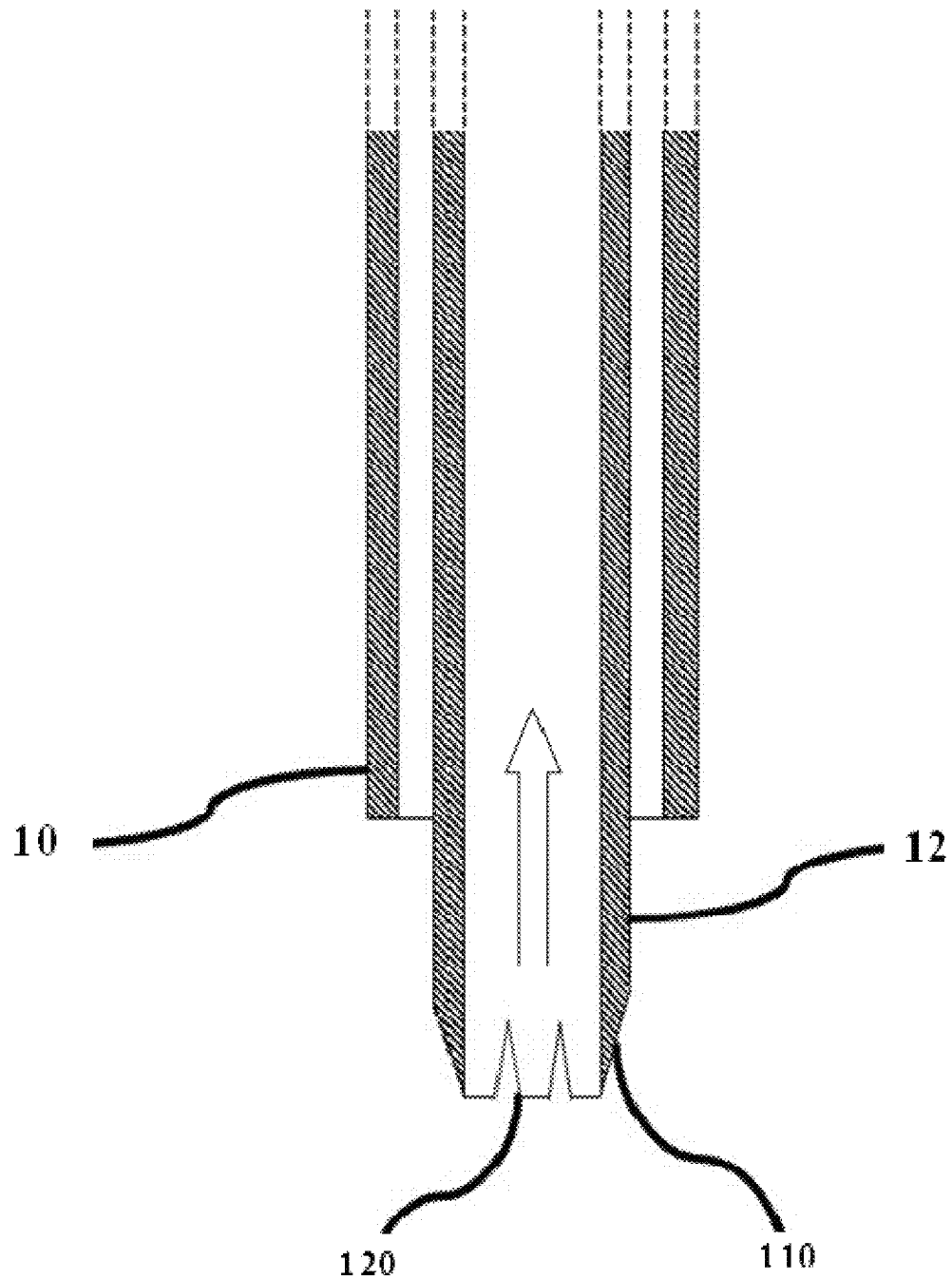
FIG. 11 is a cross-section view of the distal end of an extended cannula and suction tube of an embodiment of an the working head.

FIG. 11 is a cross-section view of the distal end of an extended cannula (10) and suction tube (12) showing a sharp round edge (110) to prevent large tissues from clogging, and saw shaped teeth (120) for enhanced tissue cutting. These teeth in combination with the high speed rotation generated by the micro-tornado forces can cut large tissue to prevent clogging of the suction tube.

Each of the above tubes or cannulas preferably have an elliptical (e.g., round) cross-section. However, other shapes are contemplated for use in the disclosed instruments.

The disclosed instruments and methods are described herein for use in dental procedures. However, these instruments can also be used in other surgical procedures for cutting and removing tissue, especially in small and difficult to reach areas.

A number of embodiments of the invention have been described. Nevertheless, it will be understood that various modifications may be made without departing from the spirit and scope of the invention. Accordingly, other embodiments are within the scope of the following claims.

What is claimed is:

1. A dental instrument, comprising a working head that generates micro-tornado forces, wherein the working head comprises:
   (a) an outer portion and an inner portion that together define a conical gap between the inner surface of the outer portion and the outer surface of the inner portion, wherein the conical gap has a base and an apex, wherein the apex is at a distal end of the working head;

(b) one or more orifices positioned at the base of the conical gap and fluidly connected to a pressurized mixture supply tube supplying a pressurized gas and abrasive mixture, wherein the one or more orifices are configured to intensify the velocity of the pressurized gas mixture;

(c) one or more sloped down grooves configured to direct the pressurized gas mixture from the one or more orifices in a conical spiral toward the apex of the conical gap;

(d) a cannula at the distal end of the working head fluidly connected to the conical gap; and (e) a suction tube extending through the center and beyond a distal end of the cannula and the inner portion.

2. The dental instrument of claim 1, wherein the suction tube is fluidly connected to a suction pump.

3. The dental instrument of claim 1, wherein the suction tube extends through the center of the inner portion and out a proximal end of the working head.

4. The dental instrument of claim 1, wherein a distal end of the suction tube comprises a sharpened edge or teeth.

5. The dental instrument of claim 1, wherein the cannula is curved.

6. The dental instrument of claim 1, further comprising a hand piece connected to a proximal end of the working head.

7. The dental instrument of claim 1, wherein the pressurized mixture supply tube is fluidly connected to a gas and abrasive powder mixing chamber.

8. The dental instrument of claim 7, wherein the gas and abrasive powder mixing chamber comprises a motorized feeder configured to feed controlled amounts of abrasive powder into a pressurized gas and powder mixing tube to produce a gas and powder mixture, wherein the pressurized gas and powder mixing tube is fluidly connected to the pressurized mixture supply tube.

9. The dental instrument of claim 8, wherein the motorized feeder comprises a rotating helix feeder.

10. The dental instrument of claim 8, wherein the gas and abrasive powder mixing chamber further comprises a hopper configured to feed the abrasive powder into the motorized feeder.

11. The dental instrument of claim 10, wherein the pressurized gas and powder mixing tube comprises a pressure equalizing hole configured to release the gas and powder mixture into the hopper in an amount sufficient to maintain pressure equilibrium.

12. The dental instrument of claim 1, wherein the pressurized mixture supply tube is fluidly connected to a gas and fluid mixing chamber.

13. The dental instrument of claim 12, wherein the gas and fluid mixing chamber comprises:

(a) a pressurized gas and fluid mixing tube fluidly connected to the pressurized mixture supply tube, and (b) a cannula fluidly connected to a fluid compartment, wherein the cannula is positioned in a constriction within the pressurized gas and fluid mixing tube configured to cause a sufficient venturi effect to draw fluid out of the fluid chamber and create a mist.

14. The dental instrument of claim 13, wherein the pressurized gas and fluid mixing tube comprises a pressure equalizing hole configured to release the mist into the fluid chamber in an amount sufficient to maintain pressure equilibrium.

15. The dental instrument of claim 1, wherein the pressurized mixture supply tube is fluidly connected to both a high pressure gas and abrasive powder mixing chamber and a high pressure gas and fluid mixing chamber by one or more check valves, selector valves, or combinations thereof.

16. The dental instrument of claim 1, further comprising an aspiration cap configured to collect tissue, fluid, and/or abrading particle residue.

17. The dental instrument of claim 16, wherein the aspiration cap comprises a dome affixed to a proximal end of the working head.

18. The dental instrument of claim 16, wherein the aspiration cap comprises a perforated aspiration tube fluidly connected to the suction tube.

19. The dental instrument of claim 1, wherein the cannula is about 1 mm to about 20 mm in length.

20. The dental instrument of claim 1, wherein conical gap is about 1.0 to about 1.5 mm in width between the inner surface of the outer portion and the outer surface of the inner portion.

21. The dental instrument of claim 1, wherein the base of the conical gap is about 4.5 to about 5.5 mm in diameter.

22. The dental instrument of claim 1, wherein the height of the conical gap from base to apex is about 5 to about 10 mm in length.

23. A method for cutting and removing decayed tissue from a tooth, comprising (a) abrading the tissue with a pressurized gas and abrasive powder mixture under micro-tornado forces using a dental instrument comprising a working head that generates micro-tornado forces, wherein the working head comprises an outer portion and an inner portion that together define a conical gap between the inner surface of the outer portion and the outer surface of the inner portion, wherein the conical gap has a base and an apex, wherein the apex is at a distal end of the working head; one or more orifices positioned at the base of the conical gap and fluidly connected to a pressurized mixture supply tube supplying the pressurized gas and abrasive powder mixture, wherein the one or more orifices are configured to intensify the velocity of the pressurized gas mixture; one or more sloped down grooves configured to direct the pressurized gas mixture from the one or more orifices in a conical spiral toward the apex of the conical gap; a cannula at the distal end of the working head fluidly connected to the conical gap; and a suction tube extending through the center and beyond a distal end of the cannula and the inner portion; and (b) excavating the tissue, fluid, and/or abrading particle residue using the dental tool.

24. The method of claim 23, wherein the micro-tornado forces are generated by forcing the pressurized gas and abrasive powder mixture at high speed around the conical gap in a conical spiral from its base to its apex.

25. The method of claim 23, wherein the pressurized gas and abrasive powder mixture under micro-tornado forces are directed through said cannula to the decayed tissue.

26. The method of claim 23, further comprising irrigating the tooth with a pressurized gas and liquid mixture under micro-tornado forces.

27. The method of claim 23, wherein the decayed tissue is selected from the group consisting of enamel, dentine, pulp.

* * * * *